US00PP17129P2

(12) United States Plant Patent
Egger

(10) Patent No.: US PP17,129 P2
(45) Date of Patent: Oct. 3, 2006

(54) *HEUCHERA* PLANT NAMED 'HOLLYWOOD'

(50) Latin Name: ***Heuchera* hybrid**
Varietal Denomination: Hollywood

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 11/155,215

(22) Filed: Jun. 15, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by silvered, dark foliage, coral flowers on short dark stalks, flowers in a wand type inflorescence, a mounding habit, and excellent vigor.

1 Drawing Sheet

Botanical denomination: *Heuchera* hybrid.
Variety designation: 'Hollywood'.

The present invention relates to a new and distinct cultivar of *Heuchera* and given the cultivar name of 'Hollywood'. *Heuchera* is in the family Saxifragaceae. *Heuchera* 'Hollywood' originated from a cross between *Heuchera* 138-1 (an unpatented, proprietary plant) as the seed parent, and *Heuchera* 37-1 (an unpatented, proprietary plant) as the pollen parent. Given its ornamental foliage and flower form it is probable that *Heuchera sanguinea, H. americana,* and *H. cylindrica* are in its parentage.

This new *Heuchera* is distinguished by:

1. Dark, round, heavily silvered foliage,
2. Large coral flowers in a wand type cluster,
3. Mounding habit,
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

BRIEF DESCRIPTION OF THE DRAWING

The drawing shows a one-year-old plant of *Heuchera* 'Hollywood' growing in a one gallon container in the greenhouse house in May in Canby, Oreg.

DETAILED PLANT DESCRIPTION

The following is a detailed description of the new *Heuchera* cultivar based on observations taken in May of a two-year-old specimen grown a two gallon container in a cold greenhouse in Canby, Oreg. This greenhouse is kept at between 55 and 85 degrees F. in the summer months and in the winter is heated to frost free, above 32 degrees F. and vented at 55 degrees F. Light intensities are consistent with full sun in Canby, Oreg. which gets 42.8 inches of rain per year and is often cloudy. Plants were hand watered when dry. The color descriptions are all based on The Royal Horticultural Society Colour Chart.

Botanical denomination: *Heuchera* hybrid.
Variety designation: 'Hollywood'.
Parentage: *Heuchera* 138-1×37-1 (both proprietary, unreleased plants).

Plant:
- *Form.*—Basal rosette, herbaceous perennial.
- *Hardiness.*—USDA Zone 4 to 9.
- *Size.*—15 cm tall from the soil level to the top of the foliage and 40 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate to orbicular.
- *Lobing.*—5 main shallow lobes.
- *Venation.*—Palmate.
- *Margins.*—Crenate, undulate.
- *Apex.*—Obtuse.
- *Base.*—Cordate, lobes strongly overlapping at the base.
- *Blade size.*—5.5 to 8 cm long and 5.5 to 7.6 cm wide.
- *Surface texture.*—Glandular on both sides.
- *Petiole size.*—11 to 12 cm and 2 mm wide.
- *Petiole texture.*—Glandular hairs.
- *Petiole color.*—Greyed Purple 183A.
- *Leaf color.*—Topside — Leaves are silver with prominent dark veins. New leaves — dark veins are closest to Brown 200A with the little more black and the rest of the leaf is veiled Grey 201A tinted with maroon, Greyed Purple 187D. Mature leaves — Are similar but lighter overall. Old leaves are less veiled and greener. Bottom side — Between Red Purple 59A and Greyed Purple 187A.

Inflorescence:

*Type.*—Thyrse with flowers congested near end and held close to the peduncle, called wand-type.

*Number of flowers.*—70 to 80 per thyrse.

*Number of thyrse in first bloom in spring.*—15.

*Peduncle.*—With no cauline leaves, 30 to 35 cm tall and 2.5 mm wide near base, Greyed Purple 187A, glandular hairs.

*Pedicel.*—3 to 4 mm long, with glandular hairs, Grayed Purple 187A.

*Bloom period.*—May in Canby, Oreg.

Flower bud:

*Size.*—3.5 mm wide and 6 mm long.

*Description.*—Glandular, ovoid.

*Color.*—Red 53C.

Flower:

*Type.*—Perfect, zygomorphic.

*Shape.*—Campanulate.

*Size.*—7 mm deep and 10 mm wide.

*Corolla description.*—5 in number, inconspicuous, 2.5 mm long and 1 mm wide, Red Purple 63C on both sides, spatulate with a clawed base, apex acute, margins entire, both sides glandular.

*Calyx description.*—7 mm deep and 10 mm wide, 5 lobes, divided ½ way to the base, glandular on both sides, apex acute, margins entire.

*Calyx and flower color.*—On the back side Red 53A at both ends and Red 63D in the middle. On the inside the lobes are Red 53 A to C from tip to base and the hypanthium is Red 52D.

*Stamen description.*—5, sterile, no pollen produced, filaments 1 mm long, White 155A, anthers less than 1 mm long, Greyed Orange 165A.

*Pistil description.*—Yellow 2C overall, 4 mm long, style 3 mm long.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm long.

*Color.*—Black 202A.

Pest and disease tolerance: Excellent disease resistance to powdery mildew, the common problem of *Heuchera.* Susceptible to *Heuchera* rust and root weevils.

COMPARISON TO SIMILAR *HEUCHERA*

Compared to *Heuchera* 'Strawberry Candy' (U.S. Plant Pat. No. 12,195), this new variety has larger leaves that are burgundy rather than green in color. They both have large coral pink flowers and a wand type inflorescence. The new variety has flowers that turn darker with maturity.

Compared to *Heuchera* 'Vesuvius' (U.S. Plant Pat. No. 13,215) or *Heuchera* 'Cherries Jubilee' (U.S. Plant Pat. No. 11,377), the new variety has shorter flower stems, a better veil, a wand type rather than a regular inflorescence, and larger flowers.

Compared to its seed parent, *Heuchera* 138-1, the new variety has short numerous short flowering stems of large, coral colored flowers in wand type clusters, instead of small cupped white flowers on medium length stems. The new variety has dark, heavily silvered foliage while the pollen parent had very dark foliage with a slight silver veil.

Compared to its pollen parent, *Heuchera* 37-1, the new variety has dark silvered leaves rather than green veiled leaves and large coral flowers rather than very large, red flowers. Both have wand type flowering stems.

I claim:

1. A new and distinct hybrid of *Heuchera* plant as herein illustrated and described.

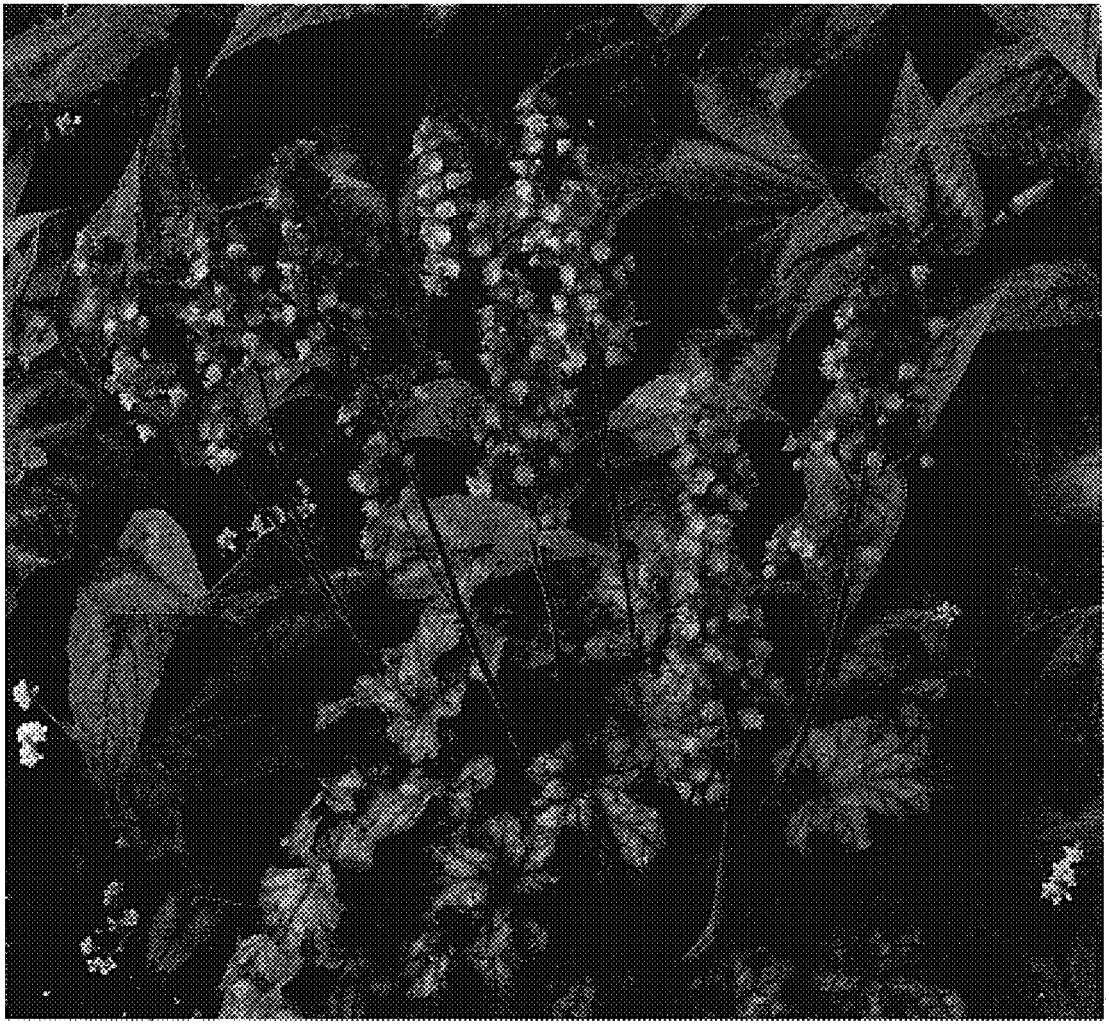

* * * * *